United States Patent [19]

Tatumoto et al.

[11] Patent Number: 5,522,979
[45] Date of Patent: Jun. 4, 1996

[54] STRATIFIED CERAMIC BODY, OXYGEN SENSOR USING THE SAME AND FABRICATION METHOD THEREOF

[75] Inventors: Hirohiko Tatumoto, Kariya; Shouzo Tanida, Anjo; Hiroshi Furuhashi; Tomio Sugiyama, both of Nagoya, all of Japan

[73] Assignee: Nippondenso Co., Ltd., Kariya, Japan

[21] Appl. No.: 424,080

[22] Filed: Apr. 19, 1995

[30] Foreign Application Priority Data

Apr. 19, 1994 [JP] Japan .................................... 6-104473
Feb. 23, 1995 [JP] Japan .................................... 7-035162

[51] Int. Cl.$^6$ ................................................ G01N 27/26
[52] U.S. Cl. .................. 204/429; 204/426; 427/124; 427/125; 427/126.2; 427/126.3; 427/126.4; 428/570; 428/212; 428/304.4; 501/81
[58] Field of Search .................................. 204/426, 429; 428/570, 577, 613, 640, 650, 58, 114, 212, 223, 304.4; 427/124, 125, 126.2, 126.3, 126.4; 501/81

[56] References Cited

U.S. PATENT DOCUMENTS 4,582,657  4/1986  Shibata et al. .......................... 204/429
5,110,442  5/1992  Kojima et al. .......................... 204/429
5,171,721  12/1992 Nanataki et al. ......................... 501/81

FOREIGN PATENT DOCUMENTS 5-10918   1/1993  Japan .
5148039   6/1993  Japan .

*Primary Examiner*—Bruce F. Bell
*Attorney, Agent, or Firm*—Cushman, Darby & Cushman

[57] ABSTRACT

An oxygen sensor has alumina porous layer on a surface of a solid electrolyte to cover electrodes and the alumina porous layer is simultaneously baked with the solid electrolyte. The alumina porous layer has baking contraction percentage which is the same range of the solid electrolyte. Alumina powder which is a starting material of the alumina porous layer includes 0.3 to 0.5 μm of a 50% grain size, 0.4 to 1.1 μm of a 70% grain size, and 0.8 to 4.0 μm of a 90% grain size in a grain size distribution of weight integration frequency and further a specific surface area according to a BET method is approximately 8.5 to 11.0 m$^2$/g. It is preferable that the baking contraction percentages of the solid electrolyte and alumina porous layer are approximately 16 to 22%.

10 Claims, 5 Drawing Sheets

STRATIFIED CERAMIC BODY, OXYGEN SENSOR USING THE SAME AND FABRICATION METHOD THEREOF

CROSS REFERENCE TO RELATED APPLICATIONS

This application is based upon and claims priority from Japanese Patent Application No. Hei 6-104473 filed Apr. 19, 1994 and Japanese Patent Application No. Hei 7-35162 filed Feb. 23, 1995, with the contents of each document being incorporated herein by reference.

BACKGROUND OF THE INVENTION

1. Field of the Invention

The present invention relates to a stratified ceramic body, oxygen sensor using the same and a fabrication method thereof.

2. Description of the Related Art

Generally, the air-fuel ratio of an engine for an automobile is measured by an oxygen sensor amidst exhaust gas components to detect the oxygen concentration thereof.

As an oxygen sensor, there conventionally exists for example an oxygen sensor of laminate type which integrates a solid electrolyte which becomes a main part of a sensing portion and a heater to heat the solid electrolyte.

This oxygen sensor has a pair of electrodes on both sides of the solid electrolyte. In order to protect the electrode which is positioned on the exhaust gas side, a porous protecting film is formed on a surface of the solid electrolyte to cover the electrode.

The foregoing protecting film is formed by plasma spraying of spinel powder onto the priorly baked surface of the solid electrolyte and the surface of the exhaust gas side electrode.

According to the foregoing method of the prior art, baking process of the solid electrolyte and formation process of the protecting film are performed separately, and so become a major factor for making the production process of the oxygen sensor complex.

For this reason, demand has increased for a simultaneous baking of a protecting film and a solid electrolyte in an oxygen sensor. However, the foregoing simultaneous baking necessitates coordination of the baking shrinkage rate of the protecting film and solid electrolyte, and realization is difficult.

Furthermore, it is essential that the protecting film formed on the exhaust gas side electrode of the oxygen sensor cause measured gas to pass and to reach the measured gas side electrode, and for this reason porosity is demanded. Meanwhile, it is demanded that the solid electrolyte be dense. Therefore, it is necessary that the protecting film and solid electrolyte not only allow simple simultaneous baking but also obtain a predetermined pore ratio in the protecting film after simultaneous baking, and simultaneous baking of the protecting film and solid electrolyte becomes even more difficult.

Accordingly, an oxygen sensor which employs ceramic starting material composed of secondary particles structured by cohesive bonding of primary particles as a protecting film of the electrode and which adjusts the baking shrinkage rate and grain size of the ceramic starting material by means of the grain size of the respective primary and secondary particles has been proposed conventionally (Japanese Patent Application Laid-open No. Hei 5-148039).

However, in this oxygen sensor as well, adjustment of the foregoing primary particles and secondary particles is still difficult.

SUMMARY OF THE INVENTION

It is an object of the present invention to provide a stratified ceramic body wherein simultaneous baking of a support body and protecting film are possible and further wherein warp and peeling of them are not generated, an oxygen sensor using the same and a fabrication method thereof.

In one preferred mode of the present invention, a stratified ceramic body includes a support body and an alumina porous layer formed by means of alumina powder baked simultaneously with the support body, the support body and alumina porous layer being mutually joined, employing technical means whereby the alumina porous layer has a baking shrinkage rate of 16% to 22% within an identical range for the support body, and further in a grain size distribution of weight integration frequency of the alumina powder which is a starting material of the alumina porous layer, a 50% grain size is 0.3 to 0.5 µm, a 70% grain size is 0.4 to 1.1 µm, and a 90% grain size is 0.8 to 4.0 µm, and still further a specific surface area according to a BET method is 8.5 to 11.0 $m^2/g$.

The invention detailed above is preferably further characterized in that the alumina porous layer is formed on a surface of the support body.

The invention further preferably employs technical means whereby the simultaneous baking temperature is 1,300° to 1,600° C.

In accordance with a preferred embodiment, the stratified ceramic body of the invention has a pore rate of the alumina porous layer is 5% to 30%.

In accordance with another preferred mode of the invention an oxygen sensor is provided having a first surface exposed to a measured gas and a second surface exposed to a reference gas, and further formed into a solid electrolyte to generate output signals corresponding to oxygen concentration within the measured gas, a measured gas side electrode and reference gas side electrode formed respectively on the first surface and the second surface of the solid electrolyte, and the first surface of the solid electrolyte being so as to cover the measured gas side electrolyte, employing technical means whereby the alumina porous layer has a baking shrinkage rate of 16% to 22% within an identical range for the support body, and in a grain size distribution of weight integration frequency of the alumina powder which is a starting material of the alumina porous layer, a 50% grain size is 0.3 to 0.5 µm, a 70% grain size is 0.4 to 1.1 µm, and a 90% grain size is 0.8 to 4.0 µm, and further a specific surface area according to a BET method is 8.5 to 11.0 $m^2/g$.

In the above described embodiment the simultaneous baking temperature is preferably 1,300° to 1,600° C.

A pore rate of the alumina porous layer of the oxygen sensor, is preferably 5% to 30%.

The invention further relates to a fabrication method for an oxygen sensor comprising a step wherein partially stabilized zirconia powder composed of zirconia and yttria series is formed to a predetermined configuration to obtain a solid electrolyte formed body of which a baking shrinkage rate is within a range of 16% to 22%, a step to mix an organic binder with alumina powder to obtain a porous layer formed body with a sheet configuration, a step to apply an electrode paste which becomes porous after baking to a surface of the solid electrolyte formed body, a step to dispose the porous formed body on a surface of the solid electrolyte formed body so as to cover the electrode paste, and a step to bake the entirety of the porous formed body, the electrode paste, and the solid electrolyte formed body within a temperature range of 1,300° to 1,600° C., employing technical means whereby in a grain size distribution of weight integration frequency of the alumina powder which is a starting material of the alumina porous layer, a 50% grain size is 0.3 to 0.5 µm, a 70% grain size is 0.4 to 1.1 µm, and a 90% grain size is 0.8 to 4.0 µm, and further a specific surface area according to a BET method is 8.5 to 11.0 m²/g.

In the above method technical means are preferably employed whereby the solid electrolyte formed body is provided with a first surface exposed to measured gas and a second surface exposed to reference gas, and the electrode paste is formed on the first surface.

The inventive method is preferably further characterized in that it employs a simultaneous baking temperature of 1,300° to 1,600° C.

As an incidental comment, according to the present invention, in a case where 50% grain size is less than 0.3 µm, a case where 70% grain size is less than 0.4 µm, or a case where 90% grain size is less than 0.8 µm in grain size distribution of weight integration frequency of the alumina powder, the problem occurs wherein the pore ratio of the alumina porous layer becomes small, passage of measured gas becomes insufficient, and sensor response becomes poor. Conversely, in a case where 50% grain size exceeds 0.5 µm, a case where 70% grain size exceeds 1.1 µm, or a case where 90% grain size exceeds 4.0 µm, the baking shrinkage rate of the alumina porous layer becomes small, and the occurrence of warpage and peeling between the alumina porous layer and support body becomes likely.

In a stratified ceramic body according to the present invention, alumina powder which is a starting material of the porous layer structuring the alumina porous layer has a 50% grain size, 70% grain size, and 90% grain size in a grain size distribution of weight integration frequency within the above-described ranges, and specific surface area according to the BET method is 8.5 to 11.0 m²/g. By means of establishment within this range, the alumina porous layer becomes porous in a baking temperature region of 1,400° to 1,600° C., and additionally the baking shrinkage rate of the alumina porous layer is within the same range as the baking shrinkage rate of the support body. Therefore, simultaneous baking of the alumina porous layer and support body can be performed. Additionally, warpage and peeling of the alumina porous layer and support body do not occur and the two are reliably joined, even in a case where this simultaneous baking is done. For this reason, the alumina porous layer connect function adequately as a protecting film of the support body. Additionally, an oxygen sensor employing the above-described stratified ceramic body employs the foregoing alumina porous layer as a protecting layer of a measured gas side electrode exposed to measured gas disposed on in a solid electrolyte. The alumina porous layer thereof has suitable porosity and moreover has a baking shrinkage rate within the same range as the support body. For this reason, the alumina porous layer is sealed to the solid electrolyte with no warping and with no peeling. Therefore, the alumina porous layer prevents the penetration of pollutants of the external atmosphere into the measured electrode formed on the solid electrolyte, and can cause oxygen to diffuse to the measured electrode on the solid electrolyte. For this reason, an electrode reaction is performed by means of an oxygen concentration differential between the measured electrode on the exhaust gas side and the reference electrode on the atmosphere side formed on the solid electrolyte, and electromotive force corresponding to the oxygen concentration differential thereof is obtained. Alternatively, a limit current value based on the oxygen concentration of the exhaust gas side is obtained. Consequently, oxygen concentration can be measured accurately by means of the foregoing oxygen sensor. As described above, according to the present invention, simultaneous baking of a support body and protecting film is possible, and moreover a stratified ceramic body with no occurrent of warpage or peeling between the two, an oxygen sensor employing this, and a fabrication method for the same can be provided.

DETAILED DESCRIPTION OF THE PRESENTLY PREFERRED EXEMPLARY EMBODIMENTS

Figure 7:
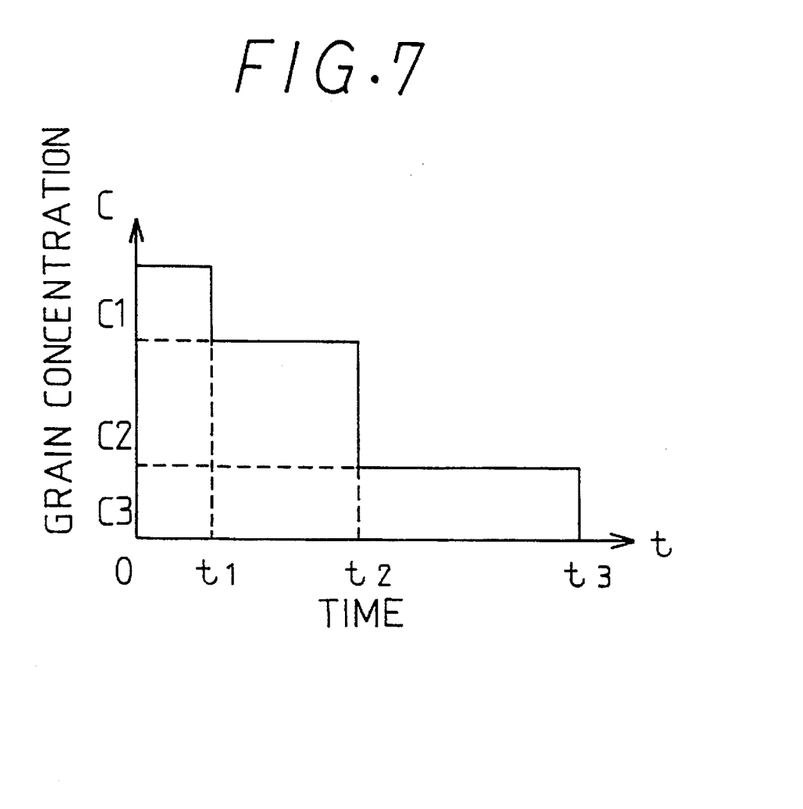
FIG. 7 is another graph indicating a portion of a measurement principle of a dispersion sedimentation method.
Figure 8:
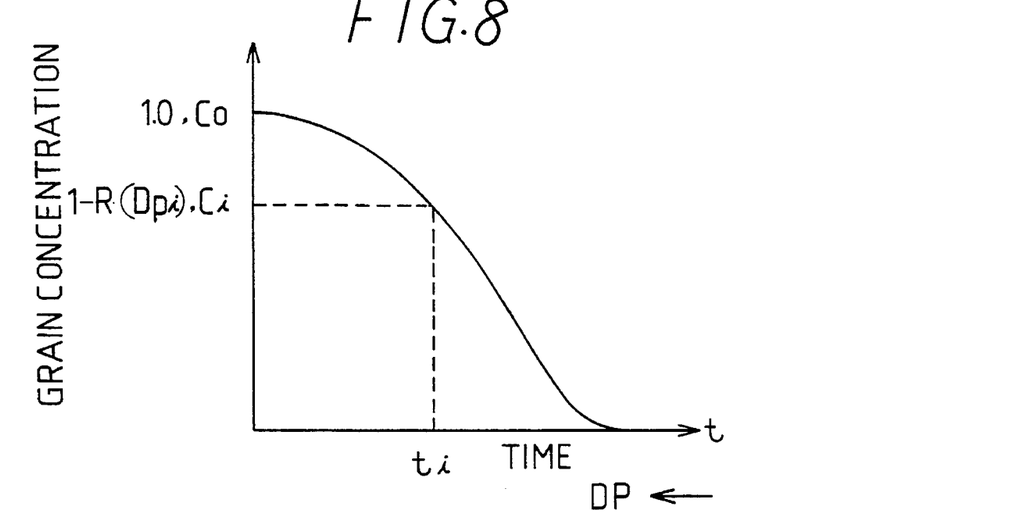
FIG. 8 is another graph indicating a portion of a measurement principle of a dispersion sedimentation method.

The measurement method of grain size distribution according to the present invention will be described. The basic measurement method of grain size distribution employed in the present invention is a grain size distribution measurement method using a sedimentation method. The measurement principle thereof utilizes the property whereby the sedimentation speed of solid grains dispersed in liquid phase differs according to the size thereof, and is a technique to determine grain size distribution by measuring grain concentration which changes temporally and spatially in a suspension. For example, in a case of polydisperse system wherein grain size differs such as the alumina powder of the present invention, if grain sizes thereof are taken to be $Dp1$, $Dp2$, and $Dp3$ (where $Dp1>Dp2>Dp3$) and times in which the respective grains orderly pass through a measurement plane shown in FIGS. 6A–D are taken to be $t1$, $t2$, and $t3$, then as shown in FIGS. 6A–D, when $t2<t<t3$ only the $Dp3$ grains are sedimented, when $t1<t\leq t2$ the $Dp2$ and $Dp3$ grains are sedimented, and when $0<t\leq t1$ the $Dp1$, $Dp2$, and $Dp3$ grains are sedimented; the grain concentration $C$ in the suspension changes at the respective times as shown in FIG. 7. Herein, if a horizontal axis is converted from time to grain size by means of Equation 1 (Stokes' law) and the concentration of a vertical axis is made dimensionless at initial concentration $C_0$, it becomes the minus sieve integration frequency, and so the change in concentration becomes the integration distribution without modification, as shown in FIG. 8.

$$Dpi = \sqrt{\frac{18\mu}{g(\rho P - \rho l)} \frac{H}{t}} \qquad \text{EQUATION 1}$$

wherein

Dpi: Grain size which is sedimented to a position of depth H from the liquid level in time t g: Gravitational acceleration ρp: Grain density ρl: Liquid density μ: Liquid viscosity A specific measurement method employing the present invention will be described hereinafter. The measurement apparatus utilizes a sedimentation type Sedigraph 5100 model made by Micromeritec Company. This apparatus measures quantitative change (grain concentration in a suspension) at a certain depth after a uniform time as the degree of passage of X-rays, and determines grain size distribution by means of changes in passing X-ray intensity.

For example, if sample grains are caused to be dispersed and X-rays are penetrated at a position of depth H from the liquid surface, the Lambert-Beer law of the following equation is realized between the incident X-ray intensity $I_0$ and penetrating X-ray intensity $I(t)$.

$$I(t) = I_0 \cdot e^{-kC} \qquad \text{EQUATION 2}$$

wherein C is grain concentration in the suspension in time t and k is a constant.

Grain concentration in time t is related to the plus sieve integration frequency R (Dpi) based on weight reference by the following equation.

$$C = C_0\{1 - R(Dpi)\} \qquad \text{EQUATION 3}$$

wherein $C_0$ is initial concentration. By means of rewriting Equations 2 and 3, grain size distribution is determined by means of the following equation.

$$1 - R(Dpi) = \frac{1}{kC_0} \ln \frac{I_0}{I(t)} \qquad \text{EQUATION 4}$$

wherein ln is a natural logarithm. Moreover, in a case of percentage expression the value determined by Equation 4 is multiplied by 100%.

Figure 5:
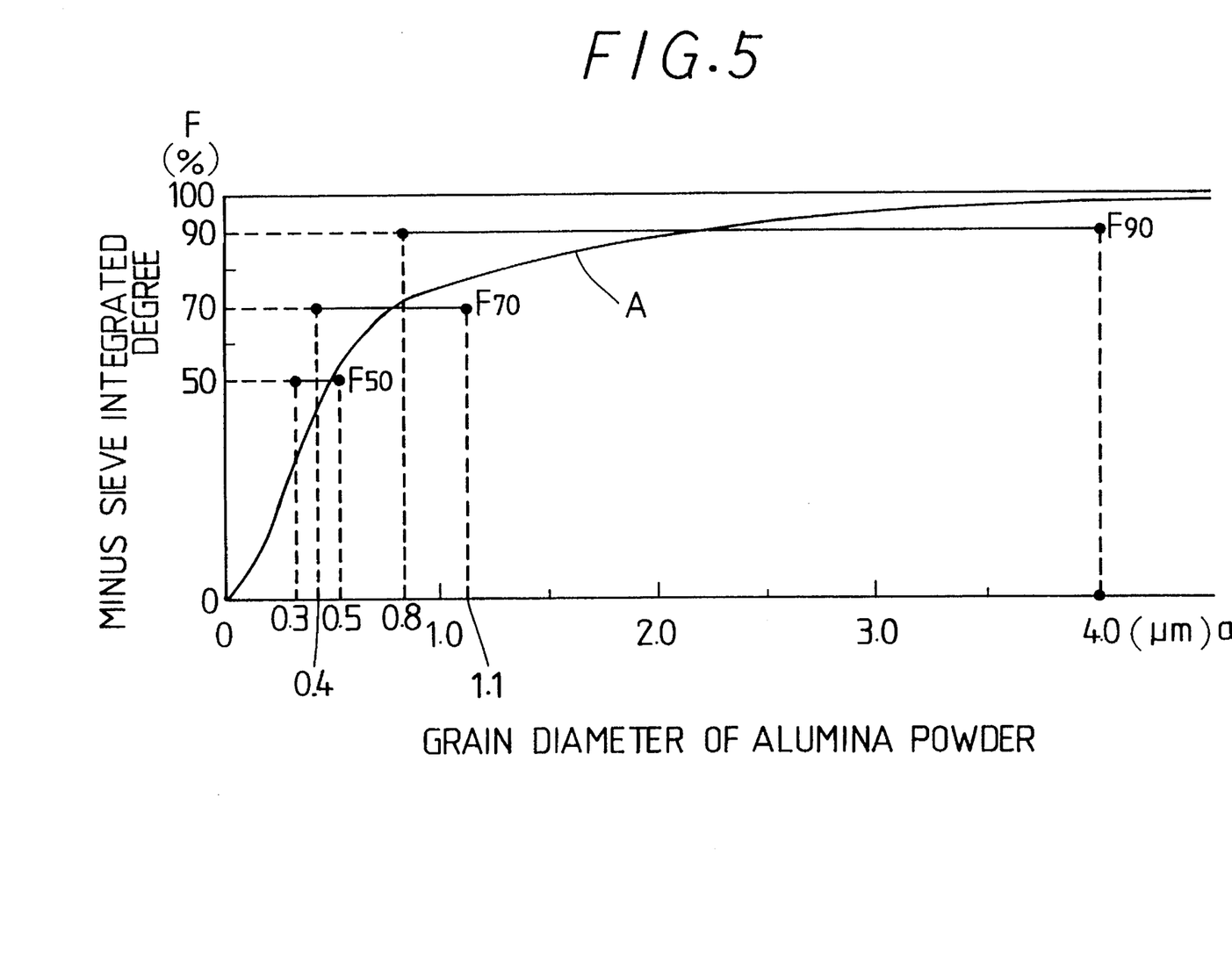
FIG. 5 is a graph indicating grain diameter of alumina powder and minus sieve integrated degree according to the present embodiment.
Figure 6A:
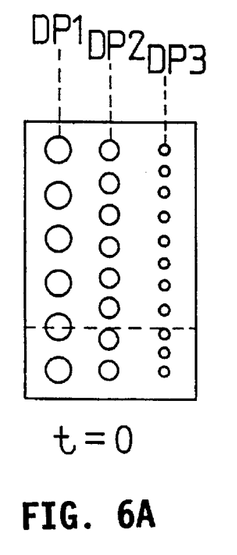
FIGS. 6A–D are graphs indicating a portion of a measurement principle of a dispersion sedimentation method.
Figure 6B:
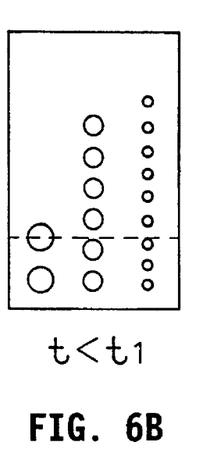
Figures 6C, 6D:
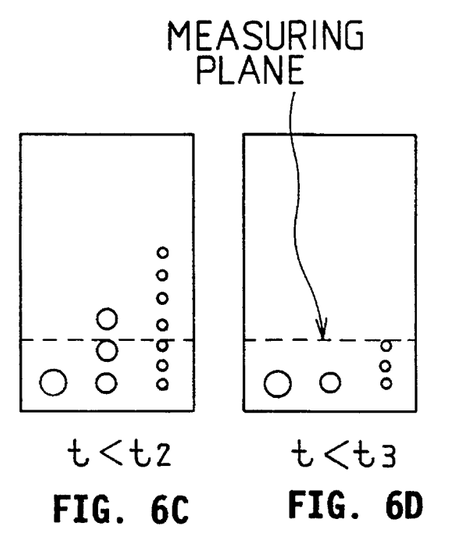

Accordingly, in FIG. 5 the vertical axis expresses the minus sieve integrated degree (%) of Equation 4 and the horizontal axis expresses Dpi of Equation 1.

The measurement method (BET method) of specific surface area will be described next. Specific surface area is surface area per unit of matter, and refers to weight reference specific surface area in a case where weight is taken as a reference. In a case where "specific surface area" alone is stated, it nearly always refers to the former, and "specific surface area" stated in this specification for the present invention is also weight reference specific surface area.

As a measurement method of specific surface area, the present invention employs a physical adsorption method (BET method) of a gas adsorption method. The basic principle of this gas adsorption method will be described next.

Briefly, the specific surface area of the sample is determined by means of actually measuring the adsorption amount of gas to the sample, converting to monomolecular layer adsorption amount in accordance with the BET equation which will be indicated next, further converting this to the number of adsorbed molecules, and multiplying by the sectional area occupied by a single adsorbed molecule on the surface of the sample. "Specific surface area" ($m^2/g$) refers to surface area per 1 g of the sample.

The foregoing measurement method causes molecules of known size to be adsorbed on the surface of a powder sample, and determines the specific surface area from the adsorption amount thereof. The basic equation of this method is the BET equation, that is to say, the polymolecular layer theoretical equation of Brunauer, Emmett, and Terrer. The BET formula is the following equation, where saturated vapor pressure of the adsorption material is taken to be $P_0$, pressure of adsorption equilibrium is taken to be P, and an adsorption amount at that time is taken to be V.

$$\frac{P}{V(P_0 - P)} = \frac{1}{VmK} + \frac{K-1}{VmK} \cdot \frac{P}{P_0} \qquad \text{EQUATION 5}$$

wherein, Vm is the monomolecular adsorption amount and K is a constant.

Figure 9:
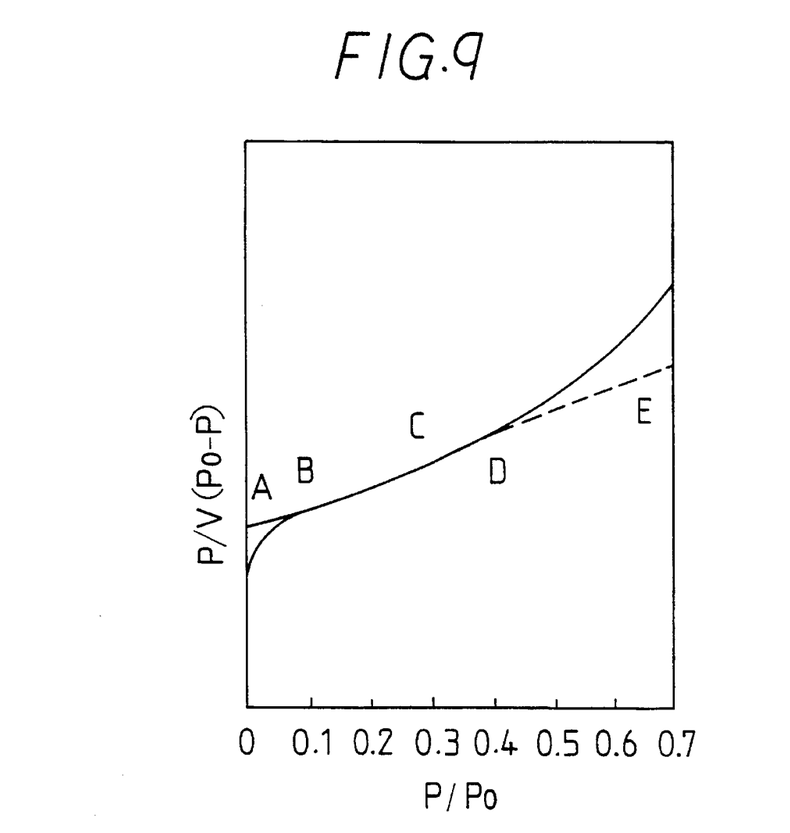
FIG. 9 is a graph indicating a portion of a measurement principle of specific surface area.

In the foregoing Equation 5, if $\{P/V(P_0-P)\}$ and $(P/P_0)$ are taken to be the vertical axis and horizontal axis of FIG. 9, Vm and K are determined from an intercept and slope of the lines thereof. Furthermore, it is confirmed that Equation 5 is effective when $(P/P_0)$ is within the range of 0.05 to 0.35.

In a case where constant K in Equation 5 is for example nitrogen adsorption, a large value is obtained. Consequently, Equation 5 becomes approximately the next equation.

$$\frac{P}{V(P_0 - P)} = \frac{1}{Vm} \cdot \frac{P}{P_0} \qquad \text{EQUATION 6}$$

wherein, Vm can be calculated when one set of P and V are determined. This is termed the single point method. In this case, it is acceptable if measured at a place where $(P_0-P)$ is about 0.3. Meanwhile, a method taking the starting point of the line of the adsorption isothermal curve (see FIG. 9) as adsorption amount Vm (the value of point B in FIG. 9) is widely used as a simple method to determine Vm.

Accordingly, if the monomolecular adsorption amount Vm is determined and the exclusive surface area σ of one adsorption molecule is known, the specific surface area of the powder sample is obtained by the following equation.

$$S = VmN\sigma \qquad \text{EQUATION 7}$$

wherein, N is Avogadro's number ($6.02 \times 10^{23}$), and Vm is expressed with mol unit.

The foregoing is the measurement principle of powder specific surface area by means of the adsorption method. According to this adsorption method, molecules are adsorbed to cracks, fissures, holes, and the like on the powder grain surface, and so the size of the entire grain surface can be measured.

According to the present invention, the specific surface area of alumina powder is 8.5 $m^2/g$ to 11.0 $m^2/g$. In a case of less than 8.5 $m^2/g$, a baking shrinkage rate may become small or a pore ratio may become larger than the target. Conversely, in a case where 11.0 $m^2/g$ is exceeded, the baking shrinkage rate may become large or the pore ratio may become smaller than the target.

The foregoing specific surface area of the alumina powder is determined by means of the above-described BET method utilizing a measurement device (see Table 1) made by Micromeritec Company.

According to the present invention, an alumina porous layer and support body are simultaneously baked. It is preferred that the temperature of the simultaneous baking be 1,300° to 1,600° C. In a case of less than 1,300° C., baking is insufficient and so a chance exists that the pore ratio may become smaller than the target. Conversely, in a case where 1,600° C. is exceeded, baking becomes excessive, pores in the alumina porous layer disappear, and a chance exists that the target cannot be satisfied. Moreover, a preferred range is 1,400° C. to 1,500° C.

According to the present invention, the baking shrinkage rate of the foregoing support body and alumina porous layer is established within a range of 16% to 22%. In a case of less than 16%, baking of the support body and porous layer is insufficient, and there is a chance of strength insufficiency or an excessively large pore ratio. Conversely, in a case where 22% is exceeded, a chance exists that the pore ratio taken to be the target may not be obtained. Moreover, a preferred range is 17% to 20%.

According to the present invention, a pore ratio of the foregoing alumina porous layer of 5% to 30% is preferred. In a case of less than 5%, diffusion speed of the fluid passing through the alumina porous layer may decline. Conversely, in a case where 30% is exceeded, strength of the alumina porous layer may decline and become susceptible to peeling from the support body.

According to the present invention, alumina, cordierite, and the like in a catalyst carrier or solid electrolyte in an oxygen sensor as will be described later exist as the foregoing support body. Zirconia is employed as a main ingredient of the foregoing solid electrolyte, and MgO, CaO, $Y_2O_3$, and $CeO_2$ are employed as stabilizing agents. However, from the standpoint of conductivity and corrosion resistance in particular, employment of partially stabilized zirconia of $Y_2O_3$-$ZrO_2$ series is preferred.

As the foregoing electrode, platinum (Pt), rhodium (Rh), or hafnium (Hf) with zirconia ($ZrO_2$) mixed therein or an alloy combining these as desired is employed. Additionally, it is preferred that the electrode be porous. By means of this, diffusion of the measured fluid to the solid electrolyte can be promoted.

(First Embodiment)

An oxygen sensor according to an embodiment of the present invention will be described hereinafter with reference to FIGS. 1 and 2.

Figure 1:
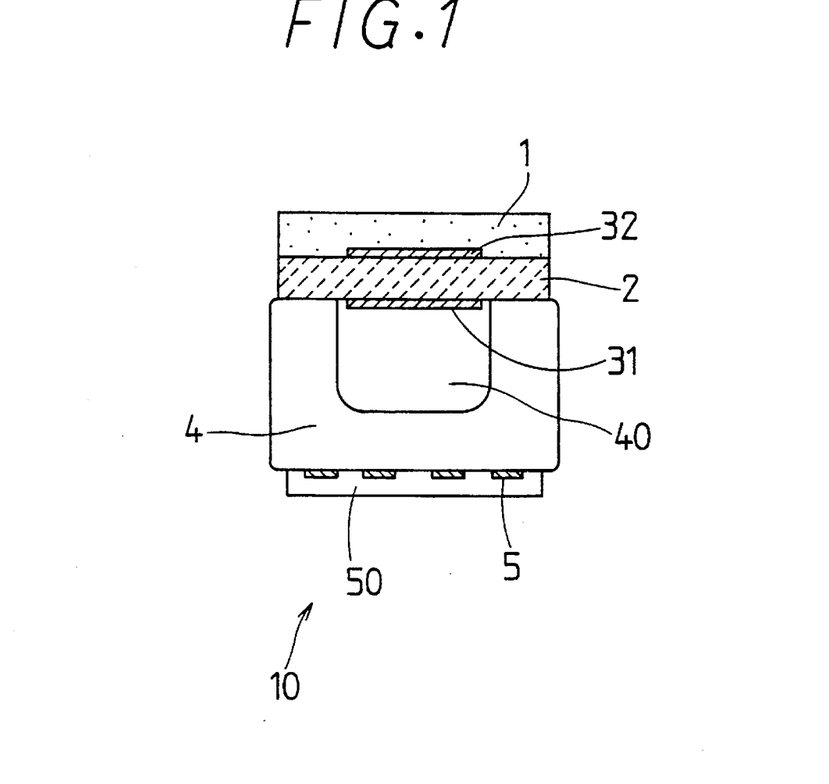
FIG. 1 is an explanatory drawing of an oxygen sensor of laminate type according to a first embodiment.

As shown in FIG. 1, an oxygen sensor according to the present embodiment is an oxygen sensor 10 of laminate type integrating a heater 5 and solid electrolyte 2 of a sensing portion. The oxygen sensor 10 has a pair of electrodes 31 and 32 provided on both sides of the solid electrolyte 2, and an alumina porous layer 1 formed on a surface of the solid electrolyte 2 so as to cover the electrode 32 of the outer side. The alumina porous layer 1 is baked simultaneously with the solid electrolyte 2 and the electrodes 31 and 32 formed on the solid electrolyte 2.

Figure 2:
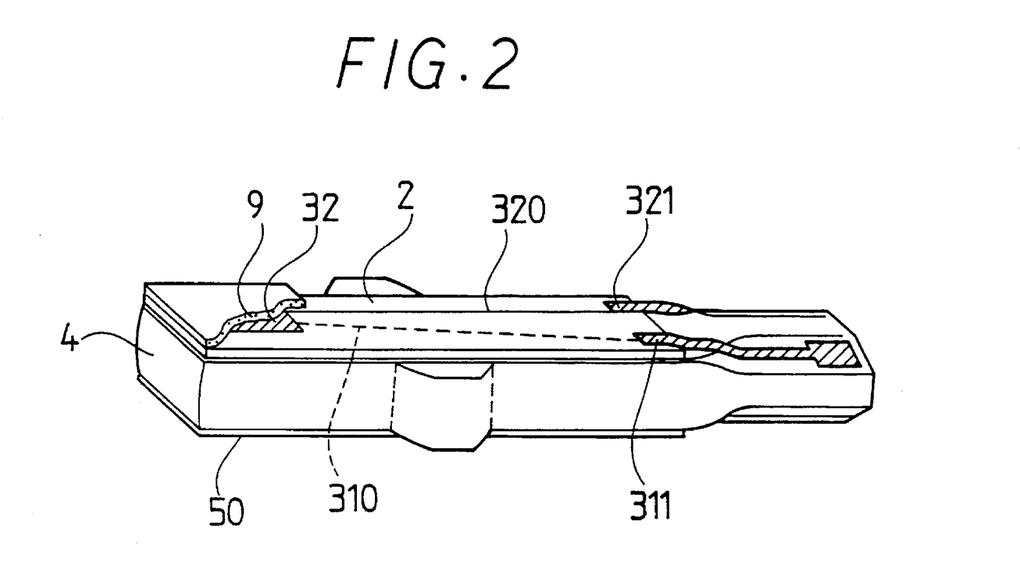
FIG. 2 is a perspective view of an oxygen sensor of laminate type according to the first embodiment.

As shown in FIG. 2, the electrodes 31 and 32 are connected to terminals 311 and 321 via lead wires 310 and 320.

The alumina porous layer 1 is a protecting film for the electrode 32 disposed on the solid electrolyte 2, and the solid electrolyte 2 is a support body of the alumina porous layer 1. The solid electrolyte 2 is partially stabilized zirconia of $Y_2O_3$-$ZrO_2$ series. The electrode 31 is a reference gas side electrode, and the electrode 32 is a measured gas side electrode. The electrode 31 is formed on a surface of a side of the solid electrolyte 2 which is exposed to reference gas, and the electrode 32 is formed on a surface of a side of the solid electrolyte 2 which is exposed to measured gas. The two electrodes are porous platinum.

The heater 5 is formed, after baking, on a surface of a sheet for heater use 50 composed of dense alumina. An insulating layer 4 whereon is formed an atmosphere induction port 40 for the purpose of introducing air to the electrode 31 is interposed between the solid electrolyte 2 and the sheet for heater use 50.

A fabrication method for the foregoing oxygen sensor 10 will be described next.

Firstly, partially stabilized zirconia of $Y_2O_3$-$ZrO_2$ series is compounded with a binder and a plasticizer and formed into a sheet configuration to obtain a pre-baked sheet to be employed in the solid electrolyte 2. The binder is polyvinyl butyral, and the plasticizer is dibutyl phthalate.

Next, the electrodes 31 and 32 are printed on both sides of the sheet of the solid electrolyte 2. The electrodes 31 and 32 have a catalytic effect and are a platinum paste which becomes porous after baking.

Additionally, a compound of alumina, plasticizer, and binder is formed into a sheet configuration to obtain a pre-baked sheet 50 for heater. The alumina starting material employed in this sheet for heater is powder of which 50% grain size in grain size distribution of weight integration frequency is 0.25 µm, and specific surface area according to the BET method is 11.0 $m^2/g$. The plasticizer is dibutyl phthalate. The binder is polyvinyl butyral.

Next, a heater 5 which is a conductive heating element is pattern-printed on this sheet 50 for heater by means of a silkscreen printing process.

Additionally, a compound of 60 wt % alumina powder, 10 wt % organic binder, 10 wt % plasticizer, and 20 wt % organic solvent for the purpose of formation of the alumina porous layer is formed in a sheet configuration to make a pre-baked sheet to be employed in the alumina porous layer 1.

The alumina starting material employed in this sheet for heater is powder of which, in grain size distribution of weight integration frequency, 50% grain size is 0.37 µm, 70% grain size is 0.57 µm, and 90% grain size is 2.3 µm, and moreover specific surface area according to the BET method is 9.4 $m^2/g$.

The organic binder is polyvinyl butyral. The plasticizer is dibutyl phthalate. The organic solvent is a compound of ethanol, 1-butanol, and 2-butanol added in equal weight.

Additionally, a pre-baked insulating layer 4 of a cross-sectional U configuration provided with an atmosphere induction port 40 is formed by means of injection molding. The insulating layer 4 is composed of alumina and binder. The alumina starting material employed in this sheet for heater use is powder of which 50% grain size in grain size distribution of weight integration frequency is 0.25 µm, and specific surface area according to the BET method is 11.0 $m^2/g$. The binder is a compound of wax and ethylene-vinyl acetate polymer, and acryl.

Next, the sheet for the solid electrolyte 2 provided with the electrodes 31 and 32 as described above is laminated on the insulating layer 4 formed in the above-described manner. Furthermore, the foregoing sheet for alumina porous layer 1 is laminated to the surface of the sheet for solid electrolyte 2 to cover the electrode 31 of the solid electrolyte 2. Additionally, the foregoing sheet 50 for heater is laminated below the insulating layer 4. Next, these are simultaneously baked at a temperature of 1,470° C. in an ordinary atmosphere. By means of this, the oxygen sensor 10 indicated in FIGS. 1 and 2 is obtained.

The foregoing oxygen sensor 10 was a favorable bond-baked device with no occurrence of warp or peeling between the solid electrolyte 2 and alumina porous layer 1. The baking shrinkage rate of the alumina porous layer 1 was 18.9%. The alumina porous layer 1 became porous by means of baking, and the pore ratio thereof was 13.3%. The baking shrinkage rate of the solid electrolyte 2 was within the range of 16 to 20%, and the mean value thereof was 18.0%. The solid electrolyte 2 and insulating layer 4 became dense by means of simultaneous baking, and the electrodes 31 and 32 became porous.

Moreover, according to the present embodiment the sheet for solid electrolyte 2, the sheet for alumina porous layer 1, the injection-molded body for insulating layer 4, and the sheet 50 for heater were respectively formed independently and subsequently these were laminated and baked simultaneously, and so control of the configurations and thicknesses of the respective members is simple and material yield is favorable. As a result, reduction of production costs for an oxygen sensor became possible.

(Comparative Example)

According to the present comparative example, an oxygen sensor was fabricated employing, as the alumina powder employed in the alumina porous layer, alumina powder having, in grain size distribution of weight integration frequency, 50% grain size of 0.61 μm, 70% grain size of 1.3 μm, and 90% grain size of 3.6 μm, and moreover a specific surface area according to the BET method of 8.8 $m^2/g$.

In the oxygen sensor obtained according to the present comparative example, the alumina porous layer peeled from the solid electrolyte. The baking shrinkage rate of the alumina porous layer was 13.2%. The baking shrinkage rate of the solid electrolyte was within the range of 16 to 20%, and the mean value thereof was 18.0%. The pore ratio of the alumina porous layer was 38.6%.

It is understood from this that the alumina porous layer peels in a case where the grain size of the alumina powder is outside the range according to the present invention, or the baking shrinkage rate of the alumina porous layer is not within the range of the baking shrinkage rate of the solid electrolyte.

(Second Embodiment)

Figure 3:
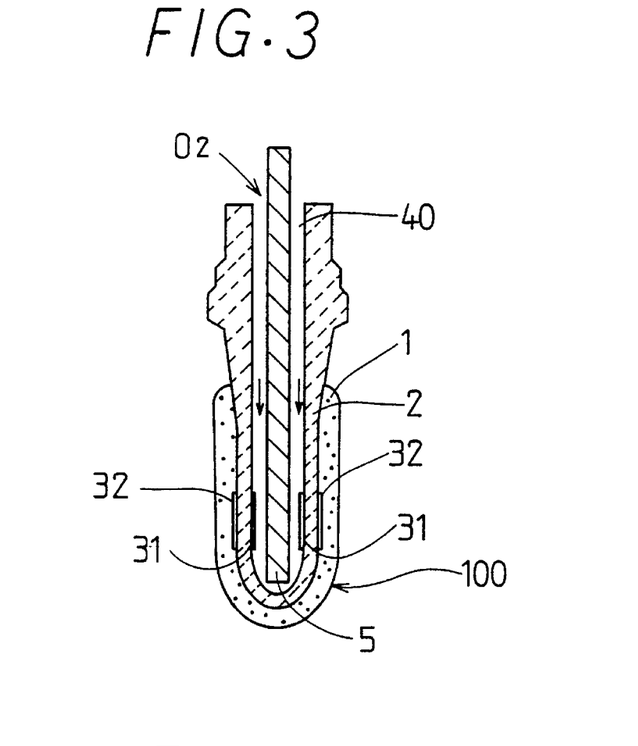
FIG. 3 is an explanatory drawing of an oxygen sensor of cup configuration according to a second embodiment.

As shown in FIG. 3, the present embodiment is an oxygen sensor 100 of cup configuration. The oxygen sensor 100 has a solid electrolyte 2 of cup configuration one end of which is open and the other end of which is closed, electrodes 31 and 32 disposed respectively on an inner side and an outer side of the solid electrolyte 2, and a heater 5 inserted fixedly into the interior of the solid electrolyte 2. An alumina porous layer 1 is formed on the surface of the solid electrolyte 2 to cover the electrode 31. The alumina porous layer 1 and solid electrolyte 2 are baked simultaneously.

A fabrication method for the foregoing oxygen sensor 100 will be described next.

Firstly, as the starting material of the porous layer, 60 wt % alumina powder is compounded with the 10 wt % organic binder, 10 wt % plasticizer, and 20 wt % organic solvent employed in the first embodiment and formed into a sheet configuration to obtain a pre-baked sheet for alumina porous layer 1 use.

In the alumina powder which is the porous layer starting material, in grain size distribution of weight integration frequency, 50% grain size is 0.30 μm, 70% grain size is 0.40 μm, and 90% grain size is 0.89 μm, and moreover specific surface area according to the BET method is 10.8 $m^2/g$.

Meanwhile, binder and water are compounded with partially stabilized zirconia of $Y_2O_3$-$ZrO_2$ series, spray-dried, and subsequently formed into a cub configuration with a dry type stamping machine to obtain the pre-baked solid electrolyte 2.

Next, the electrodes 31 and 32 are applied to the inner side surface and outer side surface of the solid electrolyte 2. The electrodes have a catalytic effect and are a platinum paste which becomes porous after baking. Thereafter, the heater 5 is inserted and fixed within the solid electrolyte 2 of cup configuration. By means of this, the oxygen sensor 100 is obtained.

The baking shrinkage rate of the alumina porous layer 1 was 17.4%, and the pore ratio was 8.4%. The baking shrinkage rate of the solid electrolyte 2 was within the range of 16 to 20%, and the mean value thereof was 19.0%. There was no occurrent of warp or peeling in the alumina porous layer 1 and solid electrolyte 2.

(Third Embodiment)

According to the present embodiment, the various alumina powders indicated in Table 1 were employed to fabricate laminate type oxygen sensors similar to that of the first embodiment. Samples 2 through 6 and, as comparative examples, comparative samples C1 and C7 through C11 according to the present invention were prepared.

Figure 4:
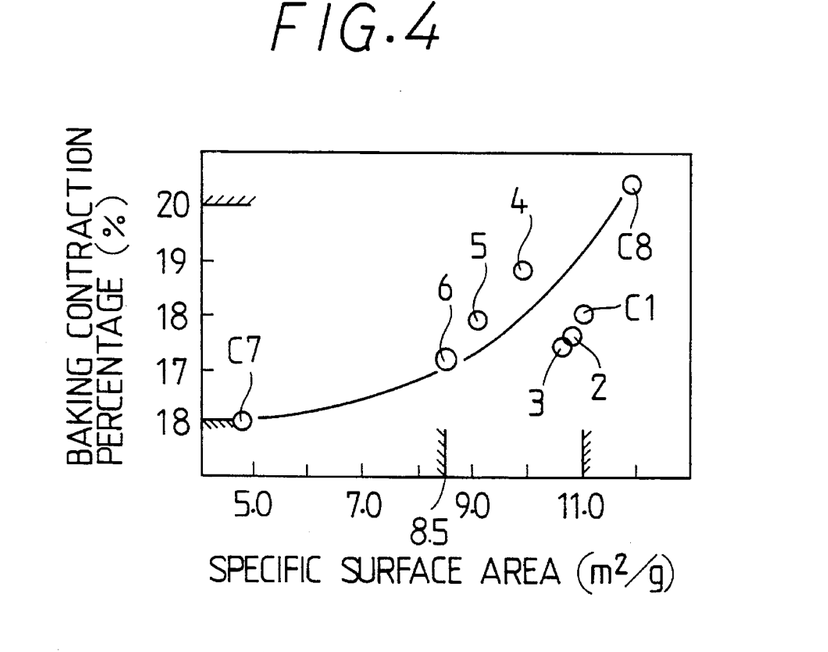
FIG. 4 is a graph indicating a relationship between a specific surface area and baking contraction percentage of alumina powder according to a third embodiment.

In the foregoing respective samples, the baking shrinkage rate and pore ratio of the alumina porous layer was measured, and the presence of warpage or peeling between the alumina porous layer and solid electrolyte was evaluated. The results thereof are indicated in Table 1. Additionally, FIG. 4 indicates the relationship between the specific surface area of the alumina powder of the porous starting material and the baking contraction percentage of the alumina porous layer for these samples.

As can be understood from Table 1, warp and peeling in the alumina porous layer and solid electrolyte did not occur in the oxygen sensors of samples 2 through 6 according to the present invention. Additionally, as can be understood from Table 1 and FIG. 4, the baking shrinkage rate of the alumina porous layer was 16.0 to 18.9%, which was a value within the same range as the baking shrinkage rate of the solid electrolyte (16.0 to 20.0%). Furthermore, the pore ratio of the alumina porous layer was 8.4 to 27.4%, and it was possible to realize diffusion of measured gas suitable for electrochemical reaction of the solid electrolyte. According to an oxygen sensor of the present invention, it was possible to measure accurately an oxygen concentration in a measured gas.

Meanwhile, in comparative sample C1, baking at a baking temperature of 1,400° to 1,500° C. proceeded too quickly because grain size of the starting material was fine, and so the alumina porous layer did not become porous and the pore ratio was 0%. Additionally, in comparative samples C8 through C11, warp and peeling occurred between the alumina porous layer and the solid electrolyte. The reason for this is that the baking shrinkage rate of the alumina powder of the porous layer starting material differed markedly from the mean baking shrinkage rate of 18.0% of the solid electrolyte, and was outside the range of the baking shrinkage rate of 16.0 to 20.0% of the solid electrolyte.

According to the foregoing results, it is understood that in a case where the alumina porous layer has a baking contraction percentage within the same range as the solid electrolyte, and moreover in a grain size distribution of weight integration frequency of the alumina powder which is a starting material of the porous layer, a 50% grain size is 0.3 to 0.5 μm, a 70% grain size is 0.4 to 1.1 μm, and a 90% grain size is 0.8 to 4.0 μm, and still further a specific surface area according to the BET method is 8.5 to 11.0 $m^2/g$, a favorable bond-baked body with no warpage or peeling between the alumina porous layer and solid electrolyte can be obtained.

TABLE 1

|  | Sample | 50% particle size (μm) | 70% particle size (μm) | 90% particle size (μm) | Specific surface area (m²/g) | Pore ratio (%) | Baking shrinkage rate (%) | Evaluation | Determination |
|---|---|---|---|---|---|---|---|---|---|
| Comparative example | C1 | 0.25 | 0.35 | 0.79 | 11.0 | 0 | 18.0 | No pores | x |
| Present invention | 2 | 0.30 | 0.40 | 0.89 | 10.8 | 8.4 | 17.4 | No problem | o |
|  | 3 | 0.33 | 0.43 | 1.8 | 10.1 | 10.6 | 17.3 | ↑ | o |
|  | 4 | 0.37 | 0.57 | 2.3 | 9.4 | 13.3 | 18.9 | ↑ | o |
|  | 5 | 0.41 | 0.71 | 2.8 | 9.1 | 20.5 | 17.9 | ↑ | o |
|  | 6 | 0.47 | 1.1 | 2.8 | 8.6 | 27.4 | 17.2 | ↑ | o |
| Comparative examples | C7 | 0.55 | 0.66 | 0.88 | 4.9 | 11.8 | 16.0 | ↑ | o |
|  | C8 | 0.35 | 0.38 | 1.0 | 11.9 | 10.5 | 20.6 | Slight warpage present | Δ |
|  | C9 | 0.61 | 1.3 | 3.6 | 8.8 | 38.6 | 13.2 | Large warpage | x |
|  | C10 | 0.76 | 1.3 | 4.2 | 10.2 | 30.3 | 14.8 | Large warpage | x |
|  | C11 | 0.95 | 1.2 | 2.0 | 3.5 | 36.9 | 9.7 | Occurrence of peeling | x |

Specific surface area of alumina powder determined by means of the BET method utilizing a Furosobu II 2300 model made by MicromeriTec., Co.

What is claimed is:

1. A stratified ceramic body, comprising:

a support body; and an alumina porous layer formed by alumina powder baked simultaneously with said support body, said support body and alumina porous layer being mutually joined, wherein said alumina porous layer has a baking contraction percentage of 16% to 22% within an identical range for said support body, and further said alumina powder which is a starting material of said alumina porous layer includes 0.3 to 0.5 μm of a 50% grain size, 0.4 to 1.1 μm of a 70% grain size, and 0.8 to 4.0 μm of a 90% grain size in a grain size distribution of weight integration frequency and further a specific surface area according to a BET method is approximately 8.5 to 11.0 m²/g;

wherein said alumina porous layer is formed on a surface of said support body;

wherein said simultaneous baking is at a temperature of approximately 1,300° to 1,600° C.; and wherein a pore ratio of said alumina porous layer is approximately 5% to 30%.

2. A stratified ceramic body according to claim 1, wherein said simultaneous baking temperature is approximately 1,400° to 1,500° C.

3. A stratified ceramic body according to claim 1, wherein said baking contraction percentage is approximately 17 to 20%.

4. An oxygen sensor comprising:

a solid electrolyte having a first surface exposed to a measured gas and a second surface exposed to a reference gas, and generating output signals corresponding to oxygen concentration within said measured gas;

a measured gas side electrode disposed on said first surface of said solid electrolyte;

a reference gas side electrode disposed on said second surface of said solid electrolyte;

an alumina porous layer disposed on said first surface of said solid electrolyte to cover said measured gas side electrode, said alumina porous layer being made of alumina powder which is baked with said solid electrolyte simultaneously;

wherein, said alumina porous layer has a baking contraction percentage of approximately 16% to 22% within an identical range for said support body; and said alumina powder which is a starting material of said alumina porous layer includes 0.3 to 0.5 μm of a 50% grain size, 0.4 to 1.1 μm of a 70% grain size, and 0.8 to 4.0 μm of a 90% grain size in a grain size distribution of weight integration frequency and further a specific surface area according to a BET method is approximately 8.5 to 11.0 m²/g;

wherein said simultaneous baking is at a temperature of approximately 1,300° to 1,600° C.; and wherein a pore ratio of said alumina porous layer is approximately 5% to 30%.

5. A stratified ceramic body according to claim 4, wherein said simultaneous baking temperature is approximately 1,400° to 1,500° C.

6. A stratified ceramic body according to claim 4, wherein said baking contraction percentage is approximately 17 to 20%.

7. A fabrication method for an oxygen sensor, comprising the steps of:

providing a solid electrolyte formed body made of partially stabilized zirconia powder composed of zirconia and yttria series, formed to a set configuration and having a baking contraction percentage within a range of approximately 16% to 22%;

providing a porous layer formed body having a sheet configuration formed of mixing an organic binder and alumina powder;

pasting an electrode paste which becomes porous after baking to a surface of said solid electrolyte formed body;

disposing said porous formed body on a surface of said solid electrolyte formed body to cover said electrode paste; and baking the entirety of said porous formed body, said electrode paste, and said solid electrolyte formed body within a temperature range of approximately 1,300° to 1,600° C., wherein said alumina powder which is a starting material of said alumina porous layer includes 0.3 to 0.5 μm of a 50% grain size, 0.4 to 1.1 μm of a 70% grain size, and 0.8 to 4.0 μm of a 90% grain size in a grain size distribution of weight integration frequency and further a specific surface area according to a BET method is approximately 8.5 to 11.0 $m^2/g$.

8. An fabrication method for an oxygen sensor according to claim 7, wherein said solid electrolyte formed body has a first surface exposed to measured gas and a second surface exposed to reference gas, and said electrode paste is formed on said first surface.

9. An fabrication method for an oxygen sensor according to claim 8, wherein said simultaneous baking temperature in optimum condition is approximately 1,400° to 1,500° C.

10. An fabrication method for an oxygen sensor according to claim 7, wherein said simultaneous baking temperature in optimum condition is approximately 1,400° to 1,500° C.

* * * * *